United States Patent
Thiel et al.

(10) Patent No.: US 11,253,793 B1
(45) Date of Patent: Feb. 22, 2022

(54) ISOLATING COMPONENTS FROM PLANTS

(71) Applicant: UCG Holdings, LLC, Santa Rosa, CA (US)

(72) Inventors: Dylan Thiel, Santa Rosa, CA (US); Derek Thiel, Santa Rosa, CA (US); Sushanta Parikh, Santa Rosa, CA (US)

(73) Assignee: UCG Holdings, LLC, Santa Rosa, CA (US)

( * ) Notice: Subject to any disclaimer, the term of this patent is extended or adjusted under 35 U.S.C. 154(b) by 0 days.

(21) Appl. No.: 17/220,717

(22) Filed: Apr. 1, 2021

Related U.S. Application Data

(60) Provisional application No. 63/130,592, filed on Dec. 24, 2020.

(51) Int. Cl.
| | |
|---|---|
| *B01D 11/02* | (2006.01) |
| *A61K 36/18* | (2006.01) |
| *B01D 1/00* | (2006.01) |
| *B01D 17/00* | (2006.01) |

(Continued)

(52) U.S. Cl.
CPC ........ *B01D 11/0288* (2013.01); *A61K 36/185* (2013.01); *B01D 1/00* (2013.01); *B01D 11/0292* (2013.01); *B01D 17/00* (2013.01); *C07C 45/81* (2013.01)

(58) Field of Classification Search
CPC ... B01D 1/00; B01D 1/26; B01D 3/10; B01D 11/02; B01D 11/0203; B01D 11/0211; B01D 11/028; B01D 11/0288; B01D 11/292; B01D 11/0403; B01D 15/08; B01D 17/00; B01D 17/005; B01D 39/06; B01D 2011/007; A61K 36/00; A61K 36/16; A61K 36/185; A61K 36/268; A61K 36/53; A61K 36/532; A61K 36/62; A61K 36/896; A61K 36/906; A61K 36/9066; A61L 2/005; A61L 2/0011; A61L 2/0017; A61L 2/0047; A61L 2/0064; A61L 2/02; A61L 2/022; A61L 2/10; A61L 2/12; A61L 2/202; A61L 2202/21; C07C 37/004; C07C 39/23; C07C 45/78; C07C 45/79; C07C 45/81; C07C 45/82; C07C 45/85; C07C 49/248; C07C 49/255

See application file for complete search history.

(56) References Cited

U.S. PATENT DOCUMENTS

| | | |
|---|---|---|
| 10,323,014 B2 | 6/2019 | Robertson |
| 10,413,845 B1 | 9/2019 | Tegen et al. |
| 10,414,709 B1 * | 9/2019 | Tegen ............... B01D 11/0292 |

(Continued)

FOREIGN PATENT DOCUMENTS

WO    2020028991    2/2020

OTHER PUBLICATIONS

Sánchez Machado, José & Ruiz, Y & Raventós, M & Auleda, J.M. & Hernandez, Eduard. (2010). Progressive freeze concentration of orange juice in a pilot plant falling film. Innovative Food Science & Emerging Technologies—Innov Food Sci Emerg Technol. 11. 10.1016/j.ifset.2010.06.006.

(Continued)

*Primary Examiner* — Joseph W Drodge
(74) *Attorney, Agent, or Firm* — Plant & Planet Law Firm

(57) ABSTRACT

The invention relates to methods of separating or isolating a component from a plant using freeze separation. The invention includes products produced by said methods.

22 Claims, 1 Drawing Sheet

(51) Int. Cl.
*C07C 45/81* (2006.01)
*A61K 36/185* (2006.01)

(56) References Cited

U.S. PATENT DOCUMENTS

| | | | | |
|---|---|---|---|---|
| 2016/0346339 | A1* | 12/2016 | Finley | A61K 36/185 |
| 2017/0008870 | A1 | 1/2017 | Dibble | |
| 2017/0049830 | A1* | 2/2017 | Raderman | A61K 9/0014 |
| 2017/0360861 | A1* | 12/2017 | Humphreys | A61K 36/185 |
| 2019/0077781 | A1* | 3/2019 | Dijkstra | B01D 11/0296 |
| 2019/0192993 | A1 | 6/2019 | Levy | |
| 2020/0016509 | A1* | 1/2020 | Hari | A61K 36/185 |
| 2020/0080021 | A1* | 3/2020 | Thomas | B01D 5/00 |
| 2020/0147516 | A1* | 5/2020 | Hartsei | B01D 11/0207 |
| 2020/0190002 | A1* | 6/2020 | Tegen | C07C 37/685 |
| 2020/0197466 | A1 | 6/2020 | Speier | |
| 2020/0199055 | A1* | 6/2020 | Jansen | C07D 311/78 |
| 2020/0346136 | A1* | 11/2020 | Lantz | B01D 5/003 |
| 2020/0390711 | A1* | 12/2020 | Schaefer | A61K 31/352 |
| 2021/0023471 | A1* | 1/2021 | Rivas | F26B 3/347 |

OTHER PUBLICATIONS

Osorio, M., Moreno, F.L., Raventos, M., Hernández, E., Ruiz, Y., Progressive stirred freeze-concentration of ethanol-water solutions, Journal of Food Engineering (2018), doi 10.1016/j.jfoodeng.2017. 12.026.

Moreno, Teresa & Montanes, Fernando & Tallon, Stephen & Fenton, Tina & King, Jerry. (2020). Extraction of cannabinoids from hemp (*Cannabis sativa* L.) using high pressure solvents: An overview of different processing options. The Journal of Supercritical Fluids. 161. 104850. 10.1016/j.supflu.2020.104850.

* cited by examiner

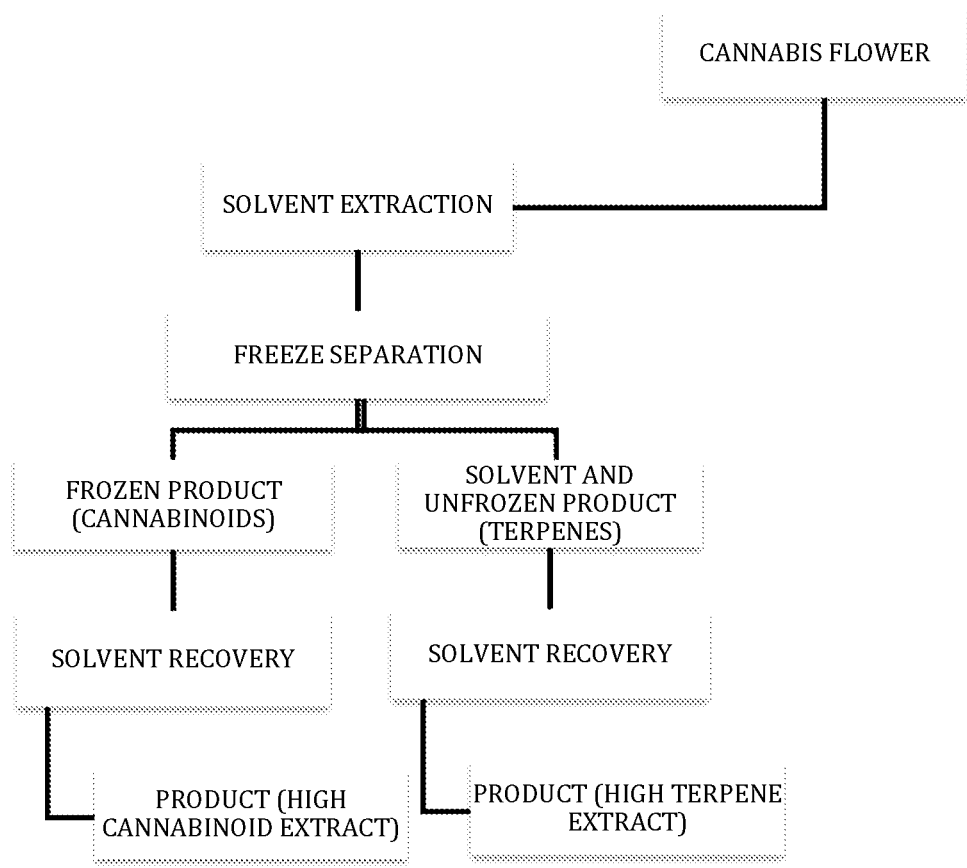

ISOLATING COMPONENTS FROM PLANTS

CLAIM OF PRIORITY

The present Application for Patent claims priority to Provisional Application No. 63/130,592, filed Dec. 24, 2020, and assigned to the assignee hereof and hereby expressly incorporated by reference herein.

BACKGROUND

Field

The present invention relates to methods of separating or isolating a component from a plant using freeze separation. The invention includes products produced by said methods.

Background

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel and medicines.

Cannabidiol (CBD) extracted from *Cannabis* is widely used in over-the-counter medicines and topical treatments and is also the active ingredient in the FDA-approved drug Epidiolex. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1093/pm/pnz227; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Likewise, *Cannabis* biochemistry produces a wide array of other classes of molecules that have medicinal promise and effects. These include terpenes, bioflavonoids, cannabinoids, flavonoids, lignin, lecithin, waxes, lipids, gums, and pigments. The future of human and animal health and well-being will be affected significantly by advances in understanding and working with the richly diverse and complex biochemistry of the *Cannabis* plant.

Therefore, there is a need to provide a method for isolating a component of interest such as a cannabinoid or a terpene from a *Cannabis* plant without degrading the component through heat, vacuum, or oxidation common in traditional separation techniques.

SUMMARY

Some embodiments of the invention relate to a method for separating a first component of interest from a second component of interest in a plant or plant part. The method can include solubilizing a plant or plant part with a solvent in which at least the first component and the second component are substantially soluble resulting in an extract solution comprising a first component in an initial first-component concentration and a second component in an initial second-component concentration. The method can include subjecting the extract solution to a temperature at which the first component and the second component differentially freeze, resulting in a solid fraction comprising the first component and a liquid fraction comprising the second component. The method can include recovering the solid fraction having a final first-component concentration that is greater than the initial first-component concentration. The method can include recovering the liquid fraction having a final second-component concentration that is greater than the initial second-component concentration.

In some embodiments, the method can further include heating the extract solution to a vaporization state of the solvent before the subjecting step.

In some embodiments, first component can be a cannabinoid, terpene or flavonoid, bioflavonoid, lecithin, or lipid and the second component can be a cannabinoid, terpene or flavonoid, bioflavonoid, lecithin, or lipid that is different from the first component.

In some embodiments, the plant is a *Cannabis* plant.

In some embodiments, the plant is a *Humulus* plant.

In some embodiments, the solvent can be a hydrocarbon solvent. In some embodiments, the hydrocarbon solvent can be liquified petroleum gas (LPG).

In some embodiments, the solvent can be a blend of multiple solvents. In some embodiments, the solvent can be a single solvent.

In some embodiments, the solvent used can be based on the polarity of the first component or the second component or both.

In some embodiments, the temperature in the subjecting step can be adjusted based upon the freezing temperatures of the first component or the second component or both.

In some embodiments, the pH of the extract solution can be adjusted based upon the first component or the second component or both.

In some embodiments, the subjecting step can occurs under pressure. In some embodiments, the pressure can be adjusted based on a property of the first component or the second component or both.

In some embodiments, the solid fraction can be subject to further freezing for differential separation and removal of one or more impurities in the fraction.

In some embodiments, the liquid fraction can be subject to freezing for differential separation and removal of one or more impurities in the fraction.

Some embodiments of the invention relate to a method for extracting a target component from a plant. The method can include (a) subjecting a solution comprising components of a plant or extract to a temperature to obtain a frozen fraction and a liquid fraction; (b) collecting the frozen fraction and the liquid fraction; (c) subjecting the liquid fraction to an evaporation step to obtain a solution with a high concentration of the target component.

In some embodiments, the method can further include subjecting the solution of (c) to a temperature below zero to obtain a frozen fraction and a liquid fraction and repeating steps (b) and (c) to obtain a final solution.

In some embodiments, the method can further include subjecting the final solution to a temperature below zero to obtain a frozen fraction and a liquid fraction and repeating steps (b) and (c) to obtain a second final solution.

In some embodiments, the target component can be selected from a terpene, cannabinoid, flavonoid, bioflavonoid, lecithin, lipid, or the like.

In some embodiments, the plant is a *Cannabis* plant.

In some embodiments, the plant is a *Humulus* plant.

In some embodiments, the temperature in the subjecting step is adjusted based upon the freezing temperature of the target component.

In some embodiments, step (a) occurs under pressure. In some embodiments, the pressure is adjusted based on a property of the target component.

Some embodiments of the invention relate to a method for separating one or more cannabinoids from one or more terpenes. In some embodiments, the method can include extracting *Cannabis* flower with a solvent in which cannabinoids and terpenes are substantially soluble, resulting in an extract solution that can include one or more cannabinoids in a first concentration and one or more terpenes in a second concentration. In some embodiments, the method can include subjecting the extract solution to a temperature at which the one or more cannabinoids can differentially freeze, resulting in a cannabinoid solid fraction, while the one or more terpenes can remain soluble, resulting in a terpene liquid fraction. In some embodiments, the method can include recovering the cannabinoid fraction having a cannabinoid concentration that can be greater than the first concentration. In some embodiments, the method can include recovering the terpene fraction having a terpene concentration that is greater than the second concentration.

In some embodiments, the solvent is a liquid petroleum gas (LPG).

In some embodiments, supercritical/subcritical CO2 extraction methods or other extraction methods are employed.

In some embodiments, the temperature can be adjusted based upon a chemical profile of the cannabinoids and the terpenes in a given source of flower.

In some embodiments, the subjecting step can include freezing the solution in or on a vessel, such that cannabinoids adhere to each other or the vessel and the terpenes remain unfrozen and can be separated by filtration before being transferred to a subsequent collection vessel.

In some embodiments, the at least one of the terpene fraction and the cannabinoid fraction can be subject to further freezing for differential separation and removal of any impurities in the fraction.

Some embodiments of the invention relate to a method for extracting a target component from a plant. In some embodiments, the method can include chilling the processed plant sample to a temperature in a container. In some embodiments, the method can include degassing the container with the processed plant sample. In some embodiments, the method can include adding a chilled solvent to the container with the processed plant sample to obtain a solution including the chilled solvent and the processed plant sample. In some embodiments, the method can include subjecting the freezing container to a temperature below OC to obtain a frozen fraction and a liquid fraction. In some embodiments, the method can include collecting the frozen fraction and the liquid fraction. In some embodiments, the method can include subjecting the liquid fraction to an evaporation step to obtain a solution with a high concentration of the target component.

In some embodiments, the subjecting and collecting steps are repeated in a second freezing container. In some embodiments the subjecting and collecting steps are repeated 2 times in a second and a third freezing container. In some embodiments, the subjecting and collecting steps can be repeated 3, 4, 5, 6, 7, or more times.

In some embodiments, the target component is a terpene (monoterpene and sequester terpene), cannabinoid, flavonoid, bioflavonoid, lecithin, lipid and/or a lignin.

In some embodiments, the plant is a *Cannabis* plant.

BRIEF DESCRIPTION OF THE DRAWINGS

FIG. 1 is a diagram depicting a method of the invention.

DETAILED DESCRIPTION

Methods of isolating and separating a component of interest from a plant or a fungus are provided.

Methods for extracting a target component from a plant are provided. The method can include subjecting a solution comprising components of a plant or extract to a temperature to obtain a frozen fraction and a liquid fraction. The method can include collecting the frozen fraction and the liquid fraction. The method can also include subjecting the liquid fraction to an evaporation step to obtain a solution with a high concentration of the target component.

In some embodiments, the component of interest or target component can be a terpene (monoterpene, sesquiterpene, diterpene), cannabinoid, flavonoid, bioflavonoid, lecithin, wax, lipid, and/or other components present within a plant, herb, or flower. In some embodiments, the plant can be any terrestrial plant. In some embodiments, the plant can be a member of the Cannabaceae family. In some embodiments, the plant can be a *Cannabis* plant. In some embodiments, the plant can be a *Humulus* plant.

The cannabinoid in any method described herein can be, for example, one or more of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-C4 (CBD-C4), cannabidivarinic acid (CBDVA), cannabidivarin (CBDV), cannabidiorcol (CBD-C1), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-C4 (THCA-C4), delta-9-tetrahydrocannabinol-C4 (THC-C4), delta-9-tetrahydrocannabivarinic acid (THCVA), delta-9-tetrahydrocannabivarin (THCV), delta-9-tetrahydrocannabiorcolic acid (THCA-C1), delta-9-tetrahydrocannabiorcol (THC-C1), delta-7-cis-iso-tetrahydrocannabivarin, delta-8-tetrahydrocannabinolic acid (Δ8-THCA), delta-8-tetrahydrocannabinol (Δ8-THC), cannabicyclolic acid (CBLA), cannabicyclol (CBL), cannabicyclovarin (CBLV), cannnabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahydro-7-hydroxyalpha-alpha-2-trimethyl-9-n-propyl-2,6-methano-2H-1-benzoxocin-5-methanol (OH-iso-HHCV), cannabiripsol (CBR) and trihydroxy-delta-9-tetrahydrocannabinol (triOH-THC), or the like.

The terpene can be, for example, a-bisabolol, borneol, a-bulnesene, camphene, camphor, 3-carene, caryophyllene oxide, b-caryophyllene, a-cedrene, citronellol, p-cymene, eucalyptol, farnsene, fenchol, fenchone, geraniol, geranyl acetate, guaiol, a-humulene, isobomeol, (−)-isopulegol, limonene, linalool, a-maaliene, b-maaliene, menthol, myrcene, nerolidol, ocimene, phellandrene, phytol, a-pinene, b-pinene, R-(+)-pulegone, sabinene, selinadiene, a-terpinene, terpinen-4-ol, a-terpineol, 4-terlineol, terpinolene, thujene, valencene, or the like.

The flavonoid can be, for example, apigenin, cannflavin A, cannflavin B, cannflavin C, chrysoeriol, cosmosiin, flavoCannabiside, kaempferol, luteolin, myricetin, orientin, isoorientin (homoorientin), quercetin, (+)-taxifolin, vitexin, and isovitexin, or the like.

In some embodiments, the method includes obtaining a plant sample from a plant or plant part. The plant sample can be any part of the plant, including, but not limited to the embryo, shoot, root, stem, meristem, seed, stipule, leaf, petal, flower bud, flower, ovule, bract, trichome, branch, petiole, internode, bark, pubescence, tiller, rhizome, frond, blade, ovule, pollen, anther, stamen, pistil, and the like, and or any combination thereof.

In some embodiments, the obtained plant sample is immediately frozen during harvest and remains frozen until after the extraction process. "Immediately" can be defined as less than 60 minutes after harvest from the plant. "Frozen" can be defined as reaching a temperature of 0 C to −90 C, or lower. For example, a plant sample can be frozen to 0 C to −90 C such that the material is frozen within about 60, 45, 30, 15, 10, 5, or 2 minutes after harvest. The plant sample can be frozen by any standard method known in the art, for example, dry ice, liquid nitrogen ethanol/iso/acetone baths, in a mechanical cooling unit, etc. In other embodiments, the plant sample is dried without freezing, for example, the plant sample is hang-dried.

In some embodiments, the frozen and/or dried plant sample is processed for extraction. The processing step can include milling, breaking down or grinding the material. The processing step can result in a composition of particles of substantially the same size. "Substantially" can be defined as being largely but not necessarily wholly what is specified, as understood by a person of ordinary skill in the art. For example, particles with sizes within 10% of the mean size can be considered as substantially the same size.

In some embodiments, the uniform particle size can be in the range of 0.01 to 0.5 cubic inches. For example, the particle size can be 0.01, 0.1, 0.2, 0.3, 0.4, 0.5 or more cubic inches.

In some embodiments, the method can include chilling the processed composition in a container or vessel. In some embodiments, the composition is chilled to a temperature of 0 C to −90 C. For example, the composition is chilled to a temperature of about 0, −10, −20, −30, −40, −50, −60, −70, −80 or −90 C. In some embodiments, the container is comprised of stainless steel and/or the like. The composition can be chilled by any standard method known in the art, for example, dry ice, liquid nitrogen, ethanol/iso/acetone baths, in a mechanical cooling unit, etc.

In some embodiments, the method includes degassing the container containing the chilled composition. For example, the container with the chilled composition can be placed into a second vessel before evacuating the column of all air.

In some embodiments, the method includes a solubilizing step that can include introducing a chilled solvent to the degassed container. "Chilled" can be defined as a temperature of 25 C to −90 C, or lower. In some embodiments, the method can include soaking the chilled composition with the chilled solvent for a period of time. The period of time can be up to 24 hours or more. The period of time can be 0.25, 0.5, 1, 2, 3, 4, 5, 6, 7, 8, 9, 10, 11, 12, 13, 14, 15, 16, 17, 18, 19, 20, 21, 22, 23, 24 or more hours. In some embodiments, the period of time is sufficient to solubilize the target component(s) in a solution with the solvent.

The solvent used in the methods can be a hydrocarbon solvent. Solvents used in the invention can include, but not be limited to, one or more of -butane, iso-butane, propane, heptane, hexane, pentane, acetone, methanol, ethanol, isopropanol, toluene, xylene, diethyl ether, chloroform, dichloromethane, and/or the like. The solvent can be liquified petroleum gas (LPG). The solubilizing step can be based on the knowledge that different solvents can interact with different components based on physical or chemical properties such as polarity. For example, the solvent used can be based on a property such as the polarity of the first component or the second component or both.

For example, solubilizing step can include solubilizing a plant or plant part with one or more of the solvents disclosed herein in which at least the first component and the second component are substantially soluble, resulting in an extract solution with a first component in an initial first-component concentration and a second component in an initial second-component concentration.

In some embodiments, the method can include optionally heating the solution. For example, the solution can be placed in a heated container. In the heated container, the solution can be warmed to a temperature and converted to a vapor state. The temperature can be a temperature sufficient to convert the solution to a vapor state. In some embodiments, the method can include collecting the vaporized solution in a collection container. In some embodiments, the heating of the solution is based upon the lowest boiling point of any component of the solution. The temperature of the heating can be as high as the boiling point of water. For example, the range can be −50, −40, −30, −20, −10, 0, 10, 20, 30, 40, 50, 60, 70, 80, 90, 100° C. The boiling points recited are based upon conditions of standard pressure A person or ordinary skill in the art will understand how to adjust temperature based on variations in pressure.

In some embodiments, the method includes monitoring the vaporized solution in the collection chamber for volume, temperature, and/or pressure. In some embodiments, the volume can be between about 1 L and 400 L. For example, the volume can be about 1, 25, 50, 75, 100, 150, 200, 250, 300, 350, 400 L, or more than 400 L, or less than 1 L. In some embodiments, the temperature can be between 0 C to −90 C. For example, the composition is chilled to a temperature of about 0, −10, −20, −30, −40, −50, −60, −70, −80 or −90 C. In some embodiments, the temperature is dependent upon the solvent that is used. For example, in some embodiments, the temperature can be between −90 C to −50 C, for propane and butane and iso-butane. In some embodiments, the pressure can be 0 to 250 psi. For example, the pressure can be 10, 25, 50, 75, 100, 125, 150, 175, 200, 225 or 250 or more psi. However, depending upon the equipment used, different pressure limits can be reached. In such embodiments, the pressure can be much higher for example 750, 1000, 1250, 1500, 1750, 2000, 2250, 2500, 2750, 3000 or more psi. With other parameters and equipment, pressures between 250 psi and 750 psi can also be employed such as, but not limited to, 300, 350, 400, 450, 500, 550, 600, 650, and 700 psi. In some embodiments, once the vaporized solution reaches a certain volume, temperature and/or pressure, the solution can be transferred to a freezing vessel.

It should be noted that in working with different solvents and extraction parameters, the person of skill in the art can vary the volume, temperature and/or pressure parameters from what has been disclosed herein. For example, in embodiments including supercritical/subcritical $CO_2$ extraction methods, the parameters can be inside or outside of the disclosed ranges.

In some embodiments, the parameters such as volume, temperature, and/or pressure are based on the target component or combination of target components.

In some embodiments, the method includes one or more freezing steps. In the freezing step, the solution can be frozen in the freezing vessel. The freezing step can occur under pressure or in a vacuum. Pressure differential can be −100 psi, −80 psi, −60 psi, −40 psi, −20 psi, −15 psi, −10 psi, −5 psi, 0 psi, 10 psi, 20 psi, 40 psi, 60 psi, 80 psi, 100 psi or more. Depending upon the equipment used, different pressure limits can be reached. In such embodiments, the pressure can be much higher for example 750, 1000, 1250, 1500, 1750, 2000, 2250, 2500, 2750, 3000 or more psi. The freezing step can occur with agitation or stirring of the solution. The stirring speed can be between 1-1000 rpm. For example, the stirring speed can be 100 rpm, 200, 300, 400, 500, 600, 700, 800, 900, 1000 or more rpm. The freezing step can include subjecting the solution to temperatures between about 0 C to −90 C for a period of time. For example, the temperature can be −10, −15, −20, −25, −30, −35, −40, −45, −50, −55, −60, −65, −70, −75, −80, −85, −90 C, or less. The period of time can be up to about 2, 4, 6, 8, 10, 12, 14, 16, 18, 20, 22, 24, 26, 28, 30, 32, 34, 36, 38, 40, 42, 44, 46, 48 hours or more. In these embodiments, separation can occur after the initial extraction/solubilization and after recovery of some of the solvent during the initial extraction. In other embodiments, the separation can happen during the initial extraction/solubilization, or directly before or after any solvent recovery. The freezing step of the invention is based on the physical principle that many different components freeze at different temperatures. Thus, the temperature can be adjusted based on the component that is targeted for extraction. For example, the freezing step can include subjecting the extract solution to a temperature at which the first component and the second component differentially freeze, resulting in a solid fraction comprising the first component and a liquid fraction comprising the second component.

In some embodiments, the freezing step produces a frozen fraction and a liquid fraction. These fractions can be separated and collected in different containers. In some embodiments, the freezing step is repeated 1, 2, 3, 4, 5, 6, 7, or more times with the liquid fraction of each preceding freezing step. The liquid fraction can subject to further freezing cycles for differential separation and removal of one or more impurities in the fraction. The frozen fraction can be collected in each freezing step. In some embodiments, the freezing step is repeated 1, 2, 3, 4, 5, 6, 7, or more times with the solid fraction. In some embodiments, the solid fraction can be subject to further freezing cycles for differential separation and removal of one or more impurities in the fraction. In some embodiments, the solid fraction is collected, thawed and re-frozen in each freezing cycle. Various conditions (e.g., temperature, duration, agitation of the solution) can be the same or can be different for each freezing step. For example, the first freezing step can be shorter that the subsequent freezing steps.

In some embodiments, each freezing step can produce a product more pure than the previous cycle. The inventive concept includes incorporating parameters such as number of freeze cycles, duration of freeze cycles, pressure, promoting or avoiding agitation, stirring speed, temperature, pH, etc. to enhance the purity of the product. The parameters can be based on a property of the component of interest/target component or combination of components of interest/target components. "Property" as used herein can be any physical or chemical property of a component, including, but not limited to freezing temperature, polarity, size, charge, acidity, alkalinity, hydrophobicity, lipophilicity, and/or the like.

In some embodiments, the frozen fraction(s) can have a higher concentration of a first components of interest, such as a cannabinoid in relation to the concentration of the initial extract sample. In some embodiments, the concentration of the first component of interest in the frozen fraction(s) can be up to 99% or more. For example, the concentration of the first component of interest can be about 10%, 15%, 20%, 25%, 30%, 35%, 40%, 45%, 50%, 55%, 60, 65, 70, 75, 80, 85, 90, 99% or more percent. After each freezing step, the concentration can increase. The liquid fraction(s) can include a solution comprising a higher concentration of a second component of interest compared to the concentration of the initial extract sample. In some embodiments, the concentration of the second component of interest can be at least 1% more than in the initial extract sample. Any different or improvement having economic value is considered sufficient to be included, for example, even 1% improvements. For example, the relative increase in concentration can be about 1, 2, 5, 10, 15, 20, 25, 50, 75, 100, 150, 200, 250, 300, 350, 400, 450, 500% or more than in the initial extract.

The frozen fraction can be subject to further isolation and extraction steps to obtain desired component(s), ratio of components or solution. For example, specific cannabinoids, terpenes, lipids or lignins can be isolated from this solution by means of additional freezing steps.

In some embodiments, cannabinoids, terpenes, lipids or lignins can be separated by freezing point and thus isolated from the solution.

The liquid fraction can be collected in a collection chamber. The collection chamber can be subject to heat and/or vacuum wherein the solvent is evaporated and recovered.

Methods for separating one or more cannabinoids from one or more terpenes are provided. In some embodiments, the method can include extracting Cannabis flower with a solvent in which cannabinoids and terpenes are substantially soluble. This can result in an extract solution comprising one or more cannabinoids in a first concentration and one or more terpenes in a second concentration. In some embodiments, the method can include subjecting the extract solution to a temperature at which the one or more cannabinoids differentially freeze, resulting in a cannabinoid solid fraction, while the one or more terpenes remain soluble, resulting in a terpene liquid fraction. In some embodiments, the method can include recovering the cannabinoid fraction having a cannabinoid concentration that is greater than the first concentration; and recovering the terpene fraction having a terpene concentration that is greater than the second concentration.

In some embodiments, the frozen fraction(s) can include a fraction comprising a higher concentration of cannabinoids in relation to the concentration of the initial extract sample.

In some embodiments, the concentration of cannabinoids in the frozen fraction(s) can be up to 99% or more of total cannabinoid. For example, the concentration of cannabinoids can be about 10%, 15%, 20%, 25%, 30%, 35%, 40%, 45%, 50%, 55%, 60, 65, 70, 75, 80, 85, 90, 99% or more percent. The liquid fraction(s) can include a solution comprising a higher concentration of terpenes compared to the terpene concentration of the initial extract sample. In some embodiments, the concentration of the second component of interest can be at least 1% more than in the initial extract sample. Any different or improvement having economic value is considered sufficient to be included, for example, even 1% improvements. For example, the relative increase in concentration can be about 1, 2, 5, 10, 15, 20, 25, 50, 75, 100, 150, 200, 250, 300, 350, 400, 450, 500% or more than in the initial extract.

Suitable solvents include, but are not limited to, n-butane, iso-butane, propane, heptane, hexane, heptane, pentane, acetone, methanol, ethanol, isopropanol, toluene, xylene, diethyl ether, chloroform, and/or dichloromethane into the vessel.

In some embodiments, the temperature can be adjusted based upon a chemical profile of the cannabinoids and the terpenes in a given source of flower.

In some embodiments, the method can include batch freezing the solution, such that the cannabinoids bond and freeze.

In some embodiments, the method can includes spraying the solution onto a surface of a heat exchanger, such that the cannabinoid fraction adheres to the heat exchanger and the terpene fraction passes over the heat exchanger for recovery in a collection vessel.

In some embodiments, the terpene fraction and/or the cannabinoid fraction can be subject to further batch freezing for differential separation and removal of any impurities in the fraction.

Products

Products produced by the methods described herein are provided.

In some embodiments, the product can have a much higher concentration of the target component(s) compared to what was present in the initial extraction sample. For example, the concentration of the component can be about 25, 50, 75, 100, 150, 200, 250, 300, 350, 400, 450, 500% or more than in the initial extract. In some embodiments, the product has enhanced properties such as increased shelf life.

EXAMPLES

Example 1

A product including a target cannabinoid is produced by differential freezing and fractionation of an extract from a *Cannabis* plant. The concentration of the cannabinoid in the product is compared to the concentration of the cannabinoid in the extract. The concentration of the cannabinoid in the product is greater than the concentration in the extract.

Example 2

A product including a target terpene is produced by differential freezing and fractionation of an extract from a *Cannabis* plant. The concentration of the terpene in the product is compared to the concentration of the terpene in the extract. The concentration of the terpene in the product is greater than the concentration in the extract.

Example 3

A product including a target lipid is produced by differential freezing and fractionation of an extract from a *Cannabis* plant. The concentration of the lipid in the product is compared to the concentration of the lipid in the extract. The concentration of the lipid in the product is greater than the concentration in the extract.

Example 4

A product including a target lignin is produced by differential freezing and fractionation of an extract from a *Cannabis* plant. The concentration of the lignin in the product is compared to the concentration of the lipid in the extract. The concentration of the lignin in the product is greater than the concentration in the extract.

Example 5

A cannabinoid is separated from a terpene by differential freezing and fractionation of an extract from a *Cannabis* plant. The concentration of the cannabinoid in the product is compared to the concentration of the cannabinoid in the extract. The concentration of the terpene in the product is compared to the concentration of the terpene in the extract. The effect of the separation is noted, in that the concentrations in the products are different from the concentrations in the extract.

Example 6

A lipid is separated from a terpene by differential freezing and fractionation of an extract from a *Cannabis* plant. The concentration of the lipid in the product is compared to the concentration of the lipid in the extract. The concentration of the terpene in the product is compared to the concentration of the terpene in the extract. The effect of the separation is noted, in that the concentrations in the products are different from the concentrations in the extract.

Example 7

A lignin is separated from a terpene by differential freezing and fractionation of an extract from a *Cannabis* plant. The concentration of the lignin in the plant is compared to the concentration of the lignin in the extract. The concentration of the terpene in the product is compared to the concentration of the terpene in the extract. The effect of the separation is noted, in that the concentrations in the extract are different from the concentrations in the extract.

Example 8

A lipid is separated from a terpene by differential freezing and fractionation of an extract from a *Cannabis* plant. The concentration of the lipid in the product is compared to the concentration of the lipid in the extract. The concentration of the terpene in the product is compared to the concentration of the terpene in the extract. The effect of the separation is noted, in that the concentrations in the product are different from the concentrations in the extract.

Example 9

Cannabinoids and terpenes were isolated and separated from a *Cannabis* flower using the methods disclosed herein. Specifically, the following protocol was used:

Once the *Cannabis* plant reached maturity, the stems and leaves were separated from the flower and discarded.

The freshly harvest flower was then frozen with dry ice within an hour of the harvest.

Once frozen, the flower was put into a stainless-steel vessel and degassed.

A blend of Iso-Butane, Propane, and N-Butane was chilled with a mechanical colling unit to −70° C. before being introduced into the stainless-steel vessel containing the flower material.

The solvent was pushed into the column until a desired pressure was reached (100 PSI) and the solvent and material were left to solubilize for a period of 10 minutes.

Once the desired soak time was reached, the solvent and solubilized cannabinoids, terpenes, and other compound (i.e. waxes, lipids) were transferred to a collection vessel where the solution was warmed to 45° C.

At this temperature the solvent was allowed to boil and turn to a vapor state where it was recovered in a separate vessel.

Once a suitable volume was reached, the solution was transferred to a secondary vessel before being cooled to −75° C. for 6 hours.

After this first cooling step, a fraction of the original solution in the vessel was frozen. The solid (frozen) fraction was enriched for cannabinoids, relative to the liquid fraction, while the remaining liquid fraction was enriched for terpenes, relative to the solid fraction.

Once the desired time was reached, the liquid fraction was transferred into a separate (tertiary) vessel and was cooled to −60° C. for 18 hours.

After this cooling step, a portion of the liquid that had been placed in the tertiary vessel was frozen. The solid (frozen) fraction was enriched for cannabinoids, relative to the liquid fraction, while the remaining liquid fraction was enriched for terpenes, relative to the solid fraction.

Once the desired time was reached, the liquid fraction was separated into another (quaternary) vessel where it went through additional cooling step for approx. 18 hours at −60° C.

Once the desired time was reach, any additional solidified compounds were separated. The solid fractions collected in other steps were combined.

After the final separation, the remaining liquid fraction was warmed to 30° C. and placed into a vacuum chamber.

Heat (30° C.) and vacuum (−25 inHg) were applied to remove residual solvents from the solution for a period of 5 days.

Once residual solvents fell below acceptable levels (under 500 ppm solvents) the terpene separation was completed.

The solidified portions of the separations were collected and set aside for further processing. The solidified portions contain waxes, lipids and cannabinoids.

The *Cannabis* flower used in this example showed the following chemical profile:

| Cannabinoid Concentration Analysis | |
|---|---|
| Cannabinoid | Result (%) |
| CBC | <0.01 |
| CBCA | <0.01 |
| CBD | <0.01 |
| CBDA | <0.01 |
| CBDV | <0.01 |
| CBDVA | <0.01 |
| CBG | <0.01 |
| CBGA | <0.01 |
| CBL | <0.01 |
| CBN | <0.01 |
| CBNA | <0.01 |
| CBT | <0.01 |
| THCA | 4.37 |
| THCV | <0.01 |
| THCVA | <0.01 |
| Delta-8 THC | <0.01 |
| Delta-9 THC | <0.01 |
| Total THC[1] | 3.83 |
| Total CBD[2] | <0.01 |
| Total Cannabinoids[3] | 4.37 |

Method: HPLC

Notes:
[1]Total THC = THCA × 0.877 + Δ9 THC.
[2]Total CBD = CBDA × 0.877 + CBD.
[3]Sum of all cannabinoids without a conversion factory applies to THCA or CBDA.

| Foreign Matter Screening | | | |
|---|---|---|---|
| Result (%) | WSLCB | Limit | Pass/Fail |
| Stems | n/a | <5 | n/a |
| Seeds | n/a | <2 | n/a |
| Other | n/a | <2 | n/a |

Method: Visual/Microscopy

| Water Activity Analysis | | | |
|---|---|---|---|
| | Result (%) | WSLCB Limit | Pass/Fail |
| Water Activity | n/a | <0.65 | n/a |

Method: Hygrometer

| Moisture Content Analysis | | | |
|---|---|---|---|
| | Result (%) | WSLCB Limit | Pass/Fail |
| Water Activity | n/a | <15 | n/a |

Method: Gravimetric

| Terpene Concentration Analysis | |
|---|---|
| Terpene | Result (%) |
| Alpha-Bisabolol | 0.1 |
| Alpha-Humulene | 0.03 |
| Alpha-Pinene | nd |
| Alpha-Terpinene | nd |
| Alpha-Terpineol | n/a |
| Beta-Caryophyllene | 0.11 |
| Beta-Myrcene | 0.04 |
| Beta-Pinene | 0.02 |
| Borneol | n/a |
| Camphene | nd |
| Citral | n/a |

Terpene Concentration Analysis

| Terpene | Result (%) |
| --- | --- |
| Citronellol | n/a |
| Delta-3-Carene | nd |
| Dihydrocarveol | n/a |
| D-Limonene | 0.09 |
| Fenchone | n/a |
| Gamma-Terpinene | nd |
| Geraniol | nd |
| Guaiol | 0.04 |
| Isopulegol | nd |
| Linalool | 0.07 |
| Nerolidol | 0.08 |
| Ocimene | nd |
| P-Cymene | nd |
| Pulegone | n/a |
| Terpinolene | nd |
| 2-Peperidinone | n/a |
| Total Terpenes | 0.58 |

Method: GC-FID

An extract with the following chemical profile was prepared from the flower:

Cannabinoid Concentration Analysis

| Cannabinoid | Result (%) |
| --- | --- |
| CBC | <0.01 |
| CBCA | <0.01 |
| CBD | <0.01 |
| CBDA | <0.01 |
| CBDV | <0.01 |
| CBDVA | <0.01 |
| CBG | <0.01 |
| CBGA | <0.01 |
| CBL | <0.01 |
| CBN | <0.01 |
| CBNA | <0.01 |
| CBT | <0.01 |
| THCA | 68.50 |
| THCV | <0.01 |
| THCVA | <0.01 |
| Delta-8 THC | <0.01 |
| Delta-9 THC | 2.58 |
| Total THC[1] | 62.65 |
| Total CBD[2] | <0.01 |
| Total Cannabinoids[3] | 71.08 |

Method: HPLC

Notes:

[1] Total THC = THCA × 0.877 + Δ9 THC.

[2] Total CBD = CBDA × 0.877 + CBD.

[3] Sum of all cannabinoids without a conversion factory applies to THCA or CBDA.

Foreign Matter Screening

| | Result (%) | WSLCB Limit | Pass/Fail |
| --- | --- | --- | --- |
| Stems | n/a | <5 | n/a |
| Seeds | n/a | <2 | n/a |
| Other | n/a | <2 | n/a |

Method: Visual/Microscopy

Water Activity Analysis

| | Result (%) | WSLCB Limit | Pass/Fail |
| --- | --- | --- | --- |
| Water Activity | n/a | <0.65 | n/a |

Method: Hygrometer

Moisture Content Analysis

| | Result (%) | WSLCB Limit | Pass/Fail |
| --- | --- | --- | --- |
| Water Activity | n/a | <15 | n/a |

Method: Gravimetric

Terpene Concentration Analysis

| Terpene | Result (%) |
| --- | --- |
| Alpha-Bisabolol | 1.09 |
| Alpha-Humulene | 0.38 |
| Alpha-Pinene | 0.09 |
| Alpha-Terpinene | nd |
| Alpha-Terpineol | n/a |
| Beta-Caryophyllene | 1.22 |
| Beta-Myrcene | 1.24 |
| Beta-Pinene | 0.19 |
| Borneol | n/a |
| Camphene | nd |
| Citral | n/a |
| Citronellol | n/a |
| Delta-3-Carene | nd |
| Dihydrocarveol | n/a |
| D-Limonene | 1.47 |
| Fenchone | n/a |
| Gamma-Terpinene | nd |
| Geraniol | nd |
| Guaiol | 0.37 |
| Isopulegol | nd |
| Linalool | 0.54 |
| Nerolidol | 0.60 |
| Ocimene | 0.08 |
| P-Cymene | nd |
| Pulegone | n/a |
| Terpinolene | nd |
| 2-Peperidinone | n/a |
| Total Terpenes | 7.26 |

Method: GC-FID

Results of the separation are provided. The frozen fraction with a higher cannabinoid concentration than the extract showed the following profile:

Cannabinoid Concentration Analysis

| Cannabinoid | Result (%) |
| --- | --- |
| CBC | <0.01 |
| CBCA | <0.01 |

| Cannabinoid Concentration Analysis | |
| --- | --- |
| Cannabinoid | Result (%) |
| CBD | <0.01 |
| CBDA | <0.01 |
| CBDV | <0.01 |
| CBDVA | <0.01 |
| CBG | <0.01 |
| CBGA | 1.32 |
| CBL | <0.01 |
| CBN | <0.01 |
| CBNA | <0.01 |
| CBT | <0.01 |
| THCA | 73.42 |
| THCV | <0.01 |
| THCVA | <0.01 |
| Delta-8 THC | <0.01 |
| Delta-9 THC | 2.93 |
| Total THC[1] | 67.31 |
| Total CBD[2] | <0.01 |
| Total Cannabinoids[3] | 77.67 |

Method: HPLC
Notes:
[1] Total THC = THCA × 0.877 + Δ9 THC.
[2] Total CBD = CBDA × 0.877 + CBD.
[3] Sum of all cannabinoids without a conversion factory applies to THCA or CBDA.

| Foreign Matter Screening | | | |
| --- | --- | --- | --- |
| | Result (%) | WSLCB Limit | Pass/Fail |
| Stems | n/a | <5 | n/a |
| Seeds | n/a | <2 | n/a |
| Other | n/a | <2 | n/a |

Method: Visual/Microscopy

| Water Activity Analysis | | | |
| --- | --- | --- | --- |
| | Result (%) | WSLCB Limit | Pass/Fail |
| Water Activity | n/a | <0.65 | n/a |

Method: Hygrometer

| Moisture Content Analysis | | | |
| --- | --- | --- | --- |
| | Result (%) | WSLCB Limit | Pass/Fail |
| Water Activity | n/a | <15 | n/a |

Method: Gravimetric

| Terpene Concentration Analysis | |
| --- | --- |
| Terpene | Result (%) |
| Alpha-Bisabolol | 1.22 |
| Alpha-Humulene | 0.19 |
| Alpha-Pinene | nd |
| Alpha-Terpinene | nd |
| Alpha-Terpineol | n/a |
| Beta-Caryophyllene | 0.63 |
| Beta-Myrcene | 0.25 |
| Beta-Pinene | 0.07 |
| Borneol | n/a |
| Camphene | nd |
| Citral | n/a |
| Citronellol | n/a |
| Delta-3-Carene | nd |
| Dihydrocarveol | n/a |
| D-Limonene | 0.54 |
| Fenchone | n/a |
| Gamma-Terpinene | nd |
| Geraniol | nd |
| Guaiol | 0.37 |
| Isopulegol | nd |
| Linalool | 0.44 |
| Nerolidol | 0.45 |
| Ocimene | nd |
| P-Cymene | nd |
| Pulegone | n/a |
| Terpinolene | 0.06 |
| 2-Peperidinone | n/a |
| Total Terpenes | 4.24 |

Method: GC-FID

The liquid fraction with a higher terpene concentration than the extract showed the following profile:

| Cannabinoid Concentration Analysis | |
| --- | --- |
| Cannabinoid | Result (%) |
| CBC | <0.01 |
| CBCA | <0.01 |
| CBD | <0.01 |
| CBDA | <0.01 |
| CBDV | <0.01 |
| CBDVA | <0.01 |
| CBG | <0.01 |
| CBGA | 1.55 |
| CBL | <0.01 |
| CBN | <0.01 |
| CBNA | <0.01 |
| CBT | 4.87 |
| THCA | 39.51 |
| THCV | <0.01 |
| THCVA | <0.01 |
| Delta-8 THC | <0.01 |
| Delta-9 THC | 1.54 |
| Total THC[1] | 36.18 |
| Total CBD[2] | <0.01 |
| Total Cannabinoids[3] | 47.46 |

Method: HPLC
Notes:
[1] Total THC = THCA × 0.877 + Δ9 THC.
[2] Total CBD = CBDA × 0.877 + CBD.
[3] Sum of all cannabinoids without a conversion factory applies to THCA or CBDA.

| Foreign Matter Screening | | | |
| --- | --- | --- | --- |
| | Result (%) | WSLCB Limit | Pass/Fail |
| Stems | n/a | <5 | n/a |
| Seeds | n/a | <2 | n/a |
| Other | n/a | <2 | n/a |

Method: Visual/Microscopy

| Water Activity Analysis | | | |
|---|---|---|---|
| | Result (%) | WSLCB Limit | Pass/Fail |
| Water Activity | n/a | <0.65 | n/a |

Method: Hydrometer

| Moisture Content Analysis | | | |
|---|---|---|---|
| | Result (%) | WSLCB Limit | Pass/Fail |
| Water Activity | n/a | <15 | n/a |

Method: Gravimetric

| Terpene Concentration Analysis | |
|---|---|
| Terpene | Result (%) |
| Alpha-Bisabolol | 2.06 |
| Alpha-Humulene | 1.55 |
| Alpha-Pinene | 0.43 |
| Alpha-Terpinene | nd |
| Alpha-Terpineol | n/a |
| Beta-Caryophyllene | 5.17 e.v. |
| Beta-Myrcene | 3.80 |
| Beta-Pinene | 0.84 |
| Borneol | n/a |
| Camphene | 0.12 |
| Citral | n/a |
| Citronellol | n/a |
| Delta-3-Carene | nd |
| Dihydrocarveol | n/a |
| D-Limonene | 5.91 |
| Fenchone | n/a |
| Gamma-Terpinene | nd |
| Geraniol | nd |
| Guaiol | 0.84 |
| Isopulegol | nd |
| Linalool | 1.82 |
| Nerolidol | 1.45 |
| Ocimene | 0.26 |
| P-Cymene | nd |
| Pulegone | n/a |
| Terpinolene | 0.23 |
| 2-Peperidinone | n/a |
| Total Terpenes | 24.48 |

Method: GC-FID

The various methods and techniques described above provide a number of ways to carry out the application. Of course, it is to be understood that not necessarily all objectives or advantages described are achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by including one, another, or several other features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, any numbers expressing quantities of ingredients, properties such as molecular weight, reaction conditions, and so forth, used to describe and claim certain embodiments of the disclosure are to be understood as being modified in some instances by the term "about." Accordingly, in some embodiments, the numerical parameters set forth in the written description and any included claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are usually reported as precisely as practicable.

In some embodiments, the terms "a" and "an" and "the" and similar references used in the context of describing a particular embodiment of the application (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Variations on preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for separating a first component of interest from a second component of interest in a plant or plant part, comprising:
    a. solubilizing a plant or plant part with a solvent in which at least the first component and the second component are substantially soluble, resulting in an extract solution comprising a first component in an initial first-component concentration and a second component in an initial second-component concentration;
    b. subjecting the extract solution to a temperature at which the first component and the second component differentially freeze, resulting in a solid fraction comprising the first component and a liquid fraction comprising the second component;
    c. recovering the solid fraction, the solid fraction having a final first-component concentration that is greater than the initial first-component concentration; and
    d. recovering the liquid fraction, the liquid fraction having a final second-component concentration that is greater than the initial second-component concentration;
    wherein the first component comprises a plurality of cannabinoids and wherein the second component comprises a plurality of terpenes,
    wherein the solid fraction is subject to further freezing for differential separation and purification of one or more cannabinoids from other one or more cannabinoids in the solid fraction, and/or, the liquid fraction is subject to freezing for differential separation and purification of one or more terpenes from other one or more terpenes in the liquid fraction.

2. The method of claim 1, further comprising heating the extract solution to a vaporization state of the solvent before step (b).

3. The method of claim 1, wherein the plant is a *Cannabis* plant.

4. The method of claim 1, wherein the plant is a *Humulus* plant.

5. The method of claim 1, wherein the solvent is a hydrocarbon solvent.

6. The method of claim 5, wherein the hydrocarbon solvent is LPG.

7. The method of claim 1, wherein the solvent is a blend of multiple solvents.

8. The method of claim 1, wherein the solvent used is based on the polarity of the first component or the second component or both.

9. The method of claim 1, wherein the temperature in the subjecting step is selected based upon the freezing temperatures of the first component or the second component or both.

10. The method of claim 1, wherein the pH of the extract solution is selected based upon the first component or the second component or both.

11. The method of claim 1, wherein the subjecting step occurs under pressure.

12. The method of claim 11, wherein the pressure is selected based on a property of the first component or the second component or both.

13. The method of claim 1, wherein the solid fraction is subject to further freezing for differential separation and removal of one or more impurities in the fraction.

14. The method of claim 1, wherein the liquid fraction is subject to freezing for differential separation and removal of one or more impurities in the fraction.

15. A method for extracting a target component from a plant comprising:
    a. subjecting a solution comprising components of a plant or extract to a temperature to obtain a frozen fraction comprising two or more cannabinoids and a liquid fraction comprising two or more terpenes;
    b. subjecting the frozen fraction to at least one additional step of further freezing to further purify at least one cannabinoid from other one or more cannabinoids in the solid fraction, and/or freezing the liquid fraction to further purify at least one terpene from other one or more terpenes in the liquid fraction; and
    c. subjecting at least one fraction from step b to an evaporation step to obtain a solution with a high concentration of at least one terpene or at least one cannabinoid.

16. The method of claim 15, further comprising subjecting the solution with a high concentration of the target component of (c) to a temperature below zero to obtain a second frozen fraction and a second liquid fraction and subjecting the second liquid fraction to a second evaporation step to obtain a final solution.

17. The method of claim 16, further comprising subjecting the final solution to a temperature below zero to obtain a third frozen fraction and a third liquid fraction and subjecting the third liquid fraction to a third evaporation step to obtain a second final solution.

18. The method of claim 16, wherein the plant is a *Cannabis* plant.

19. The method of claim 16, wherein the plant is a *Humulus* plant.

20. The method of claim 16, wherein the temperature in the subjecting step is selected based upon the freezing temperature of the target component.

21. The method of claim 16, wherein step (a) occurs under pressure.

22. The method of claim 21, wherein the pressure is selected based on a property of the target component.

* * * * *